(12) United States Patent
Kim (10) Patent No.: US 11,300,340 B2
(45) Date of Patent: Apr. 12, 2022

(54) APPARATUS FOR GENERATING REFRIGERATION FOR COOLING TARGET AND METHOD OF COOLING TARGET USING THE SAME

(71) Applicant: RECENSMEDICAL, INC., Ulsan (KR)

(72) Inventor: Gun-Ho Kim, Ulsan (KR)

(73) Assignee: RecensMedical, Inc., Ulsan (KR)

( * ) Notice: Subject to any disclaimer, the term of this patent is extended or adjusted under 35 U.S.C. 154(b) by 25 days.

(21) Appl. No.: 16/903,186

(22) Filed: Jun. 16, 2020

(65) Prior Publication Data
US 2020/0309436 A1 Oct. 1, 2020

Related U.S. Application Data

(63) Continuation of application No. PCT/KR2018/016491, filed on Dec. 21, 2018.

(30) Foreign Application Priority Data

Dec. 29, 2017 (KR) .......................... 10-2017-0184448

(51) Int. Cl.
*F25B 21/00* (2006.01)
*F25B 49/02* (2006.01)
*F25B 5/02* (2006.01)
*F25B 21/04* (2006.01)
*F24F 5/00* (2006.01)

(52) U.S. Cl.
CPC .............. *F25B 49/022* (2013.01); *F25B 5/02* (2013.01); *F25B 21/04* (2013.01); *F24F 5/0017* (2013.01); *F25B 2600/02* (2013.01)

(58) Field of Classification Search
CPC .......... F25B 21/04; F25B 49/02; F24F 5/0017
See application file for complete search history.

(56) References Cited

U.S. PATENT DOCUMENTS 2,044,823 A 6/1936 Whiteside
4,646,735 A 3/1987 Seney
(Continued)

FOREIGN PATENT DOCUMENTS

CN 2660834 Y 12/2004
EP 1 030 611 B1 9/2004
(Continued)

OTHER PUBLICATIONS

International Search Report dated Jun. 4, 2018 for PCT/KR2017/012935.
(Continued)

*Primary Examiner* — Jonathan Bradford
(74) *Attorney, Agent, or Firm* — Knobbe Martens Olson & Bear LLP (57) ABSTRACT

This application relates to an apparatus for generating refrigeration. The apparatus may include a cooling collector configured to collect cooling energy at a predetermined cooling collection temperature. The apparatus may also include a cooler thermally coupled to the cooling collector so as to cool the cooling collector. The apparatus may further include a refrigeration gate configured to block and release the collected cooling energy. The refrigeration gate may refrigerate a target region by releasing the collected cooling energy.

13 Claims, 10 Drawing Sheets

(56) References Cited

U.S. PATENT DOCUMENTS

| | | |
|---|---|---|
| 6,099,521 A | 8/2000 | Shadduck |
| 6,141,985 A | 11/2000 | Cluzeau et al. |
| 6,632,219 B1 | 10/2003 | Baranov et al. |
| 6,669,688 B2 | 12/2003 | Svaasand et al. |
| 7,037,326 B2 | 5/2006 | Lee |
| 7,780,656 B2 | 8/2010 | Tankovich |
| 7,963,959 B2 | 6/2011 | Silva et al. |
| 8,083,734 B2 | 12/2011 | Steinfatt et al. |
| D658,775 S | 5/2012 | Jiangminhui |
| 8,177,827 B2 | 5/2012 | Shapiro et al. |
| 8,256,233 B2 | 9/2012 | Boyden et al. |
| 8,409,184 B2 | 4/2013 | Baust et al. |
| 8,652,131 B2 | 2/2014 | Muller et al. |
| 8,672,879 B2 | 3/2014 | Grant et al. |
| 8,747,397 B2 | 6/2014 | Baust et al. |
| 8,788,060 B2 | 7/2014 | Nebrigic et al. |
| 8,858,583 B2 | 10/2014 | Shtram et al. |
| 9,017,318 B2 | 4/2015 | Fourkas et al. |
| 9,039,688 B2 | 5/2015 | Palmer, III et al. |
| 9,066,712 B2 | 6/2015 | Fourkas et al. |
| 9,113,855 B2 | 8/2015 | Burger et al. |
| 9,155,584 B2 | 10/2015 | Fourkas et al. |
| 9,398,975 B2 | 7/2016 | Müller et al. |
| 9,522,031 B2 | 12/2016 | Anderson et al. |
| 9,549,773 B2 | 1/2017 | Anderson et al. |
| 9,642,741 B2 | 5/2017 | Feng et al. |
| 9,801,677 B2 | 10/2017 | Anderson et al. |
| 9,855,166 B2 | 1/2018 | Anderson et al. |
| 9,956,355 B2 | 5/2018 | Besirli et al. |
| 9,974,684 B2 | 5/2018 | Anderson et al. |
| D822,841 S | 7/2018 | Cheng |
| 10,085,881 B2 | 10/2018 | Karnik et al. |
| 10,154,870 B2 | 12/2018 | Ottanelli |
| 10,188,444 B2 | 1/2019 | Fourkas et al. |
| 10,213,244 B2 | 2/2019 | Fourkas et al. |
| 10,322,248 B2 | 6/2019 | Besirli et al. |
| 10,349,997 B1 | 7/2019 | O'Reilly |
| 10,363,080 B2 | 7/2019 | Elkins et al. |
| 10,543,032 B2 | 1/2020 | Babkin et al. |
| 2004/0102768 A1 | 5/2004 | Cluzeau et al. |
| 2004/0111087 A1 | 6/2004 | Stern et al. |
| 2005/0005626 A1 | 1/2005 | McMahon |
| 2005/0059940 A1 | 3/2005 | Weber et al. |
| 2005/0261753 A1 | 11/2005 | Littrup et al. |
| 2006/0200117 A1 | 9/2006 | Hermans |
| 2006/0213509 A1 | 9/2006 | Marin et al. |
| 2007/0005048 A1 | 1/2007 | Niedbala et al. |
| 2008/0164296 A1 | 7/2008 | Shelton et al. |
| 2008/0221561 A1 | 9/2008 | Geiger et al. |
| 2009/0036846 A1 | 2/2009 | Dacquay et al. |
| 2009/0062751 A1 | 3/2009 | Newman, Jr. |
| 2009/0124972 A1 | 5/2009 | Fischer et al. |
| 2009/0149930 A1 | 6/2009 | Schenck |
| 2009/0163902 A1 | 6/2009 | DeLonzor et al. |
| 2010/0010480 A1 | 1/2010 | Mehta et al. |
| 2010/0087805 A1 | 4/2010 | Citterio et al. |
| 2010/0196343 A1 | 8/2010 | O'Neil et al. |
| 2010/0198207 A1 | 8/2010 | Elkins et al. |
| 2011/0072834 A1 | 3/2011 | Ishikura et al. |
| 2011/0098791 A1 | 4/2011 | Kim |
| 2011/0137268 A1 | 6/2011 | Thomason et al. |
| 2011/0152850 A1 | 6/2011 | Niedbala et al. |
| 2011/0177474 A1 | 7/2011 | Jamnia et al. |
| 2011/0224761 A1 | 9/2011 | Manstein |
| 2012/0130458 A1 | 5/2012 | Ryba et al. |
| 2012/0191166 A1 | 7/2012 | Callister et al. |
| 2012/0232549 A1 | 9/2012 | Willyard et al. |
| 2012/0265278 A1 | 10/2012 | Fourkas et al. |
| 2013/0116719 A1 | 5/2013 | Shtram et al. |
| 2013/0184694 A1 | 7/2013 | Fourkas et al. |
| 2013/0296811 A1 | 11/2013 | Bangera et al. |
| 2013/0315924 A1 | 11/2013 | Hsu et al. |
| 2014/0012226 A1 | 1/2014 | Hochman |
| 2014/0200511 A1 | 7/2014 | Boyden et al. |
| 2014/0277023 A1 | 9/2014 | Sekino et al. |
| 2014/0303608 A1 | 10/2014 | Taghizadeh |
| 2014/0318153 A1* | 10/2014 | Ilercil ............... F25D 11/00 62/3.3 |
| 2015/0051545 A1 | 2/2015 | Henderson et al. |
| 2016/0058488 A1 | 3/2016 | Fourkas et al. |
| 2016/0135864 A1 | 5/2016 | Babkin |
| 2016/0143802 A1 | 5/2016 | Tranfaglia et al. |
| 2016/0183996 A1 | 6/2016 | Burger et al. |
| 2016/0242956 A1 | 8/2016 | Gomez |
| 2016/0262820 A1 | 9/2016 | Allison et al. |
| 2016/0279350 A1 | 9/2016 | Besirli et al. |
| 2017/0014174 A1 | 1/2017 | Levine et al. |
| 2017/0062793 A1 | 3/2017 | Zakharyan et al. |
| 2017/0231816 A1 | 8/2017 | Ryan |
| 2017/0232243 A1 | 8/2017 | Herweijer |
| 2017/0304558 A1 | 10/2017 | Besirli et al. |
| 2017/0354451 A1 | 12/2017 | Marin et al. |
| 2018/0116705 A1 | 5/2018 | Lee et al. |
| 2018/0235805 A1 | 8/2018 | Burger et al. |
| 2018/0310979 A1 | 11/2018 | Peled et al. |
| 2019/0000524 A1 | 1/2019 | Rosen et al. |
| 2019/0015146 A1 | 1/2019 | DuBois et al. |
| 2019/0038459 A1 | 2/2019 | Karnik et al. |
| 2019/0175394 A1 | 6/2019 | Kim |
| 2019/0175395 A1 | 6/2019 | Kim |
| 2019/0175396 A1 | 6/2019 | Kim |
| 2019/0239938 A1 | 8/2019 | Kazic et al. |
| 2019/0254866 A1 | 8/2019 | Whiteley et al. |
| 2019/0290881 A1 | 9/2019 | Kim |
| 2020/0007882 A1 | 1/2020 | Abe et al. |
| 2020/0007883 A1 | 1/2020 | Toresson |
| 2020/0054483 A1 | 2/2020 | Kim |
| 2020/0100934 A1 | 4/2020 | Ariano et al. |

FOREIGN PATENT DOCUMENTS

| | | | |
|---|---|---|---|
| EP | 1892484 A1 * | 2/2008 | ............ F24F 1/022 |
| EP | 1 401 347 B1 | 8/2011 | |
| EP | 2 010 087 B1 | 11/2014 | |
| EP | 2 910 276 A1 | 8/2015 | |
| EP | 2 759 272 B1 | 11/2018 | |
| JP | 04-092663 A | 3/1992 | |
| JP | 06-086818 A | 3/1994 | |
| JP | 10-230435 A | 9/1998 | |
| JP | 2002-505155 A | 2/2002 | |
| JP | 4049358 B2 | 2/2002 | |
| JP | 2004-515270 A | 5/2004 | |
| JP | 2005-080832 A | 3/2005 | |
| JP | 2008-212638 A | 9/2008 | |
| JP | 2008-545462 A | 12/2008 | |
| JP | 2009-034273 A | 2/2009 | |
| JP | 2009-056320 A | 3/2009 | |
| JP | 2011-077314 A | 4/2011 | |
| JP | 2012-143279 A | 8/2012 | |
| JP | 2013-142410 A | 7/2013 | |
| JP | 2014-198238 A | 10/2014 | |
| JP | 2015-510802 A | 4/2015 | |
| JP | 2017-113635 A | 6/2017 | |
| KR | 20-1998-0005117 U | 3/1998 | |
| KR | 2019-980005117 U | 3/1998 | |
| KR | 10-0200669 B1 | 3/1999 | |
| KR | 10-2003-0068633 A | 8/2003 | |
| KR | 10-2004-0093706 A | 11/2004 | |
| KR | 10-0786539 B1 | 12/2007 | |
| KR | 10-0790758 B1 | 12/2007 | |
| KR | 10-2008-0045022 A | 5/2008 | |
| KR | 10-0851274 B1 | 8/2008 | |
| KR | 10-2010-0041207 A | 4/2010 | |
| KR | 10-2010-0060222 A | 6/2010 | |
| KR | 10-2010-0135863 A | 12/2010 | |
| KR | 10-1053835 B1 | 8/2011 | |
| KR | 10-2011-0119640 A | 11/2011 | |
| KR | 10-2012-0115703 A | 10/2012 | |
| KR | 10-2013-0087770 A | 8/2013 | |
| KR | 10-1366126 B1 | 2/2014 | |
| KR | 10-1386137 B1 | 4/2014 | |
| KR | 10-2014-0052667 A | 5/2014 | |
| KR | 10-2014-0069431 A | 6/2014 | |
| KR | 10-2015-0030264 A | 3/2015 | |

(56) References Cited

FOREIGN PATENT DOCUMENTS

| KR | 10-2015-0062492 A | 6/2015 |
|---|---|---|
| KR | 10-2016-0048425 A | 5/2016 |
| KR | 10-2016-0146337 A | 12/2016 |
| KR | 10-1707659 B1 | 2/2017 |
| KR | 10-1719459 B1 | 3/2017 |
| KR | 10-2017-0041776 A | 4/2017 |
| KR | 10-2017-0083399 A | 7/2017 |
| KR | 10-2017-0089842 A | 8/2017 |
| KR | 10-1813652 B1 | 8/2017 |
| KR | 10-2017-0130470 A | 11/2017 |
| KR | 10-1819204 B1 | 1/2018 |
| KR | 10-2018-0054247 A | 5/2018 |
| KR | 10-1840346 B1 | 5/2018 |
| KR | 10-1862127 B1 | 5/2018 |
| KR | 10-2018-0109828 A | 10/2018 |
| KR | 10-1936890 B1 | 1/2019 |
| KR | 10-2019-0074150 A | 6/2019 |
| WO | WO 2016/154399 A1 | 9/2016 |
| WO | WO 2018/231868 A1 | 12/2018 |

OTHER PUBLICATIONS

International Search Report dated Jul. 6, 2018 for PCT/KR2018/003773.
International Search Report dated Aug. 8, 2018 for PCT/KR2017/013901.
International Search Report dated May 30, 2019 for PCT/KR2018/016491.
International Search Report dated Mar. 27, 2020, for PCT/KR2019/017328.
Korean Notice of Allowance dated Jun. 30, 2018 for KR 10-2016-0151947.
Korean Office Action dated Oct. 22, 2018 for KR 10-2017-0162715.
Korean Office Action dated Oct. 22, 2018 for KR 10-2017-0162716.
Korean Office Action dated Jul. 29, 2019 for KR 10-2017-0162717.
Korean Notice of Allowance dated Jul. 29, 2019 for KR 10-2017-0162716.
Korean Notice of Allowance dated Aug. 29, 2019 for KR 10-2017-0162715.
Korean Office Action dated Oct. 8, 2019 for KR 10-2018-0052601—no translation avail.
Korean Office Action dated Nov. 26, 2019 for KR 10-2018-0049108—w/ Trans.
Korean Office Action dated Nov. 27, 2019 for KR 10-2018-0049109—w/ Trans.
Korean Office Action dated Dec. 6, 2019 for KR 10-2018-0049110—w/ Trans.
Korean Office Action dated Dec. 9, 2019 for KR 10-2018-0049115—w/ Trans.
Korean Office Action dated Dec. 10, 2019 for KR 10-2018-0049117—w/ Trans.
Korean Notice of Allowance dated Apr. 2, 2020 for KR 10-2018-0052601 with Eng. Translation.
Korean Office Action dated May 10, 2020 for KR10-2018-0049115, with Eng. Translation.

Office Action dated Oct. 2, 2019 for U.S. Appl. No. 15/828,449.
Office Action dated May 15, 2020 for U.S. Appl. No. 15/828,449.
Office Action dated Jun. 26, 2020 for U.S. Appl. No. 16/412,296.
Chinese First Office Action dated Dec. 22, 2020 for CN 201780083128.0.
European (EUIPO) Examination Report dated Jan. 11, 2021 for 008309504-003.
European (EUIPO) Examination Report dated Feb. 5, 2021 for 008309504-003.
International Search Report dated Mar. 4, 2021, for PCT/KR2020/012886.
International Written Opinion dated Mar. 4, 2021, for PCT/KR2020/012886.
Office Action dated Sep. 13, 2019 for U.S. Appl. No. 16/412,296.
Final Office Action dated Jan. 31, 2020 for U.S. Appl. No. 16/412,296.
Final Office Action dated Oct. 28, 2020 for U.S. Appl. No. 16/412,296.
Office Action Dated Dec. 24, 2020 for U.S. Appl. No. 17/036,269.
Office Action dated Dec. 8, 2020 for U.S. Appl. No. 17/036,311.
Notice of Allowance dated Feb. 22, 2021 for U.S. Appl. No. 17/036,311.
Office Action dated Nov. 5, 2020 for U.S. Appl. No. 29/701,630.
Notice of Allowance dated Feb. 3, 2021 for U.S. Appl. No. 29/701,630.
Office Action dated Nov. 5, 2020 for U.S. Appl. No. 29/701,631.
Notice of Allowance dated Feb. 3, 2021 for U.S. Appl. No. 29/701,631.
International Search Report and Written Opinion dated Aug. 14, 2019 for PCT/KR2019/005105.
International Search Report and Written Opinion dated Nov. 15, 2019 for PCT/KR2019/009411.
Korean Final Office Action dated Jan. 17, 2020 for KR 10-2017-0162717 with Translation.
Korean Final Office Action dated May 10, 2020, for KR 10-2018-0049109 with Translation.
Korean Notice of Allowance dated Jun. 24, 2020 for KR 10-2018-0049109—w/ Trans.
Korean Final Office Action dated May 10, 2020 for KR 10-2018-0049110—w/ Trans.
Korean Notice of Allowance dated Jun. 22, 2020 for KR 10-2018-0049110—w/ Trans.
Korean Notice of Allowance dated Jul. 21, 2020 for KR 10-2018-0049115—w/ Trans.
Korean Notice of Allowance dated May 10, 2020 for KR 10-2018-0049117.
Korean Second Office Action, with translation, dated Oct. 28, 2019 for KR 10-2018-0052601.
Korean Office Action dated Oct. 22, 2018, for KR 10-2018-0117138.
Smith et al., "Ice Anesthesia for Injection of Dermal Fillers," The American Society for Dermatologic Surgery Inc., Dermatol. Surg 2010;36:812-814, 2010.
Sarifakioglu, et al., "Evaluating the Effects of Ice Application on the Pain Felt During Botulinum Toxin Type-A Injections," Annals of Plastic Surgery, vol. 53, No. 6, Dec. 2004.

* cited by examiner

APPARATUS FOR GENERATING REFRIGERATION FOR COOLING TARGET AND METHOD OF COOLING TARGET USING THE SAME

CROSS-REFERENCE TO RELATED APPLICATIONS

This application is a continuation application of International Patent Application No. PCT/KR2018/016491 filed on Dec. 21, 2018, which claims priority to and the benefit of Korean Patent Application No, 10-2017-0184448, filed on Dec. 29, 2017, the disclosures of both of which are incorporated herein by reference in their entirety.

BACKGROUND

1. Field

This application relates to a cooling generator.

2. Discussion of Related Technology

Cooling apparatuses may be classified into a variety of forms according to driving principles thereof and generate cooling energy using a Stirling cooler, a thermodynamic cycle such as a vapor compression refrigeration cycle, liquid evaporation, or a Joule-Thomson effect using an expanding gas. Otherwise, cooling apparatuses generate cooling energy using liquid nitrogen or carbon dioxide or generate cooling energy using thermoelectric elements such as Peltier elements.

Meanwhile, when cooling is performed in a target area, since it becomes more difficult to perform cooling as a temperature decreases, conventional cooling apparatuses have a limitation in reducing a cooling time to a target cooling temperature.

SUMMARY

One aspect is a cooling generator that can perform rapid cooling to a target cooling temperature in a target area.

Another aspect is a cooling generator including a cooling accumulation unit accumulating cooling energy at a preset cooling energy accumulation temperature, a cooling unit cooling the cooling accumulation unit through thermal coupling with the cooling accumulation unit, and a cooling gate unit blocking and discharging the accumulated cooling energy. Here, the cooling gate unit cools the target area by discharging the accumulated cooling energy.

The cooling unit may be implemented using at least one of a Peltier effect, a phase change effect, a Joule-Thomson effect, and a thermodynamic cycle (cooling using a Stirling cooler or compressor). The cooling gate unit may block emission of the cooling energy through at least one of first passive cooling and active cooling while blocking emission of the cooling energy. The cooling gate unit may emit the cooling energy through at least one of second passive cooling and active heating while emitting the cooling energy.

The cooling unit may have cooling power greater than that of the cooling gate unit. The cooling accumulation unit may be a polyhedron, and a plurality of faces of the cooling accumulation unit may be thermally coupled with a cooling element included in the cooling unit. One face of the cooling accumulation unit may be thermally coupled with the cooling elements included in the cooling unit.

Another aspect is a cooling method including a first cooling operation of accumulating cooling energy by cooling a cooling energy accumulating unit thermally coupled with a cooling unit at a preset cooling energy accumulation temperature and a second cooling operation of cooling a target area to a target cooling temperature by emitting the accumulated cooling energy toward the target area.

In the first cooling operation, the target area may be maintained at a temperature different from the cooling energy accumulation temperature through at least one of first passive cooling of blocking emission of the cooling energy and active heating by a cooling gate unit thermally coupled with the cooling accumulation unit.

In the second cooling operation, the target area may be cooled at a target cooling temperature through at least one of second passive cooling performed by releasing active heating which counterbalances emission of the accumulated cooling energy from the cooling accumulation unit and active heating by a cooling gate unit thermally coupled with the cooling accumulation unit.

Another aspect is a cooling generator including a substrate where cooling is performed, one or more cooling units accumulating cooling energy at a preset cooling energy accumulation temperature, one or more cooling gate units blocking or emitting the cooling energy accumulated by the cooling units, and a cooling operation unit including an opening, which exposes a part of the substrate to the outside, and thermally coupled with the substrate to transmit the cooling energy emitted by the cooling gate unit to the substrate. Here, the cooling gate units cool the substrate through passive cooling of emitting the accumulated cooling energy and active cooling performed by the cooling gate unit.

According to embodiments, a cooling generator can perform rapid refrigeration anesthesia by intensively supplying cooling energy to a cooling medium which comes into contact with a part to be treated and performs cooling thereon.

DETAILED DESCRIPTION

Since the described technology may be variously modified and have a variety of embodiments, particular embodiments will be illustrated in the drawings and described in detail hereinafter. The effects and features of the described technology and a method of achieving the same will become clear with reference to the following embodiments which will be described below in detail with reference to the drawings. However, the present invention is not limited to the following embodiments and may be implemented in a variety of forms.

Hereinafter, embodiments will be described in detail with reference to the attached drawings. While being described with reference to the drawings, equal or corresponding components will be referred to as equal reference numerals and a repetitive description thereof will be omitted.

In the following embodiments, the terms such as first, second, and the like are used to distinguish one component from another instead of being used as limitative meanings.

In the following embodiments, singular expressions, unless clearly defined otherwise in context, include plural expressions.

In the following embodiments, the terms such as including, having, and the like mean presence of features or components disclosed in the specification and do not preclude a possibility of adding one or more features or components thereto.

In the following embodiments, when it is stated that a part such as a film, area, component, and the like is above or on another part, the part may not only be directly on the other part but may also be on the other part with still another film, area, component, and the like interposed therebetween.

In the drawings, for convenience of description, sizes of components may be exaggerated or reduced. For example, since sizes and thicknesses of components in the drawings are arbitrarily shown for convenience for description, the present invention is not limited thereto.

When any embodiments are otherwise implementable, a particular process sequence may be performed to be different from a described sequence. For example, two processes described consecutively may be performed at the same time and may be performed in an order opposite a described order.

In the following embodiments, when it is stated that films, areas, components, or the like are connected to each other, the films, areas, and components may not only be directly connected to each other but may also be indirectly connected to another film, area, and component interposed therebetween. For example, in the specification, when it is stated that films, areas, components, or the like are electrically connected, the films, areas, components, or the like may not only be directly connected to each other electrically but may also be indirectly connected to each other electrically with another film, area, component, or the like interposed therebetween.

Hereinafter, a cooling generator 70 according to some embodiments will be described in detail.

FIGS. 1 to 8 are views illustrating a technique related to a cooling generator (cooling amplification by stimulated energy of refrigeration (CASER)).

In the specification, the cooling generator 70 is applicable to medical cooling systems, and in detail, may perform a function of a cooling energy generation unit of a medical cooling apparatus. However, the concept of the present invention is not limited thereto, and the cooling generator 70 is a device that can generate and supply cooling energy and is applicable to other fields and apparatuses. The cooling generator 70 may basically generate cooling energy and cool a target object at a desired temperature while precisely cooling at high speed.

Here, the cooling generator 70 may perform a function of a CASER system.

Figure 1:
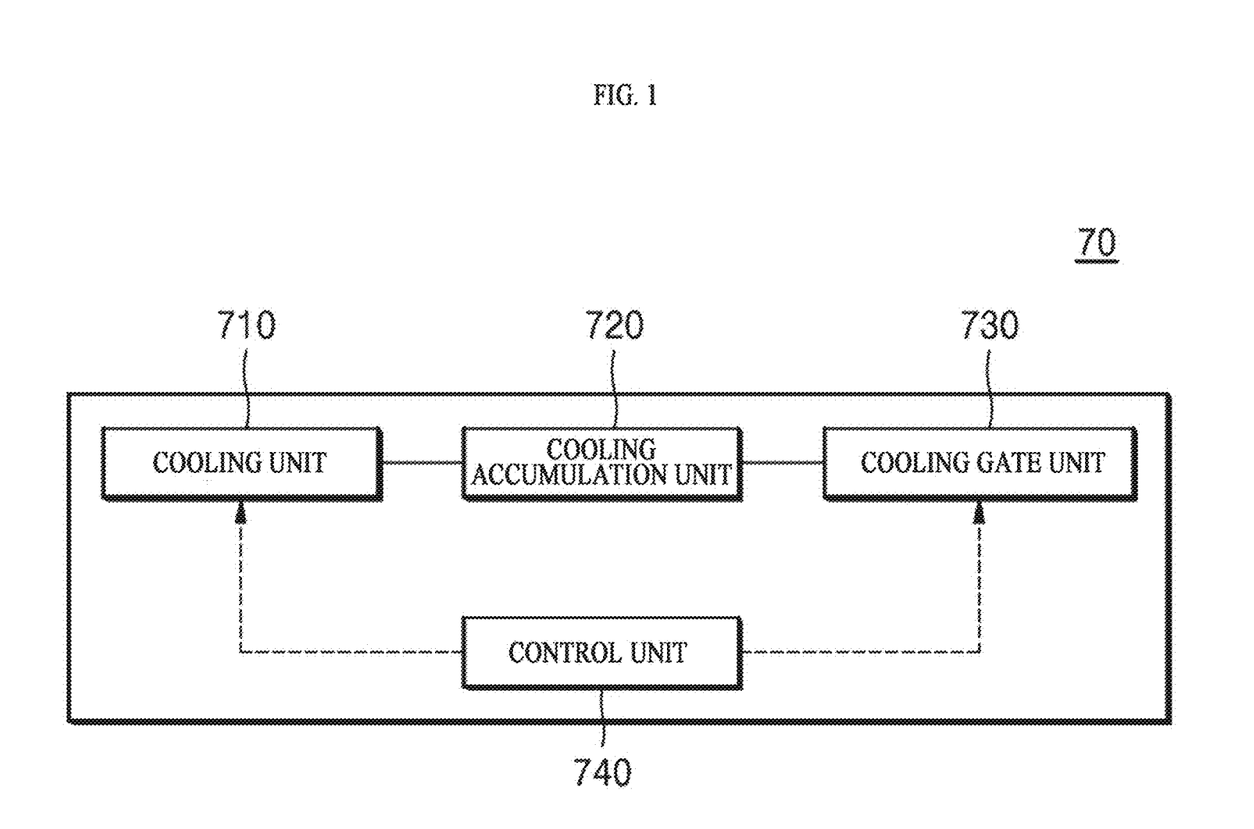
FIG. 1 is an example block diagram of a cooling generator according to some embodiments.
Figure 2:
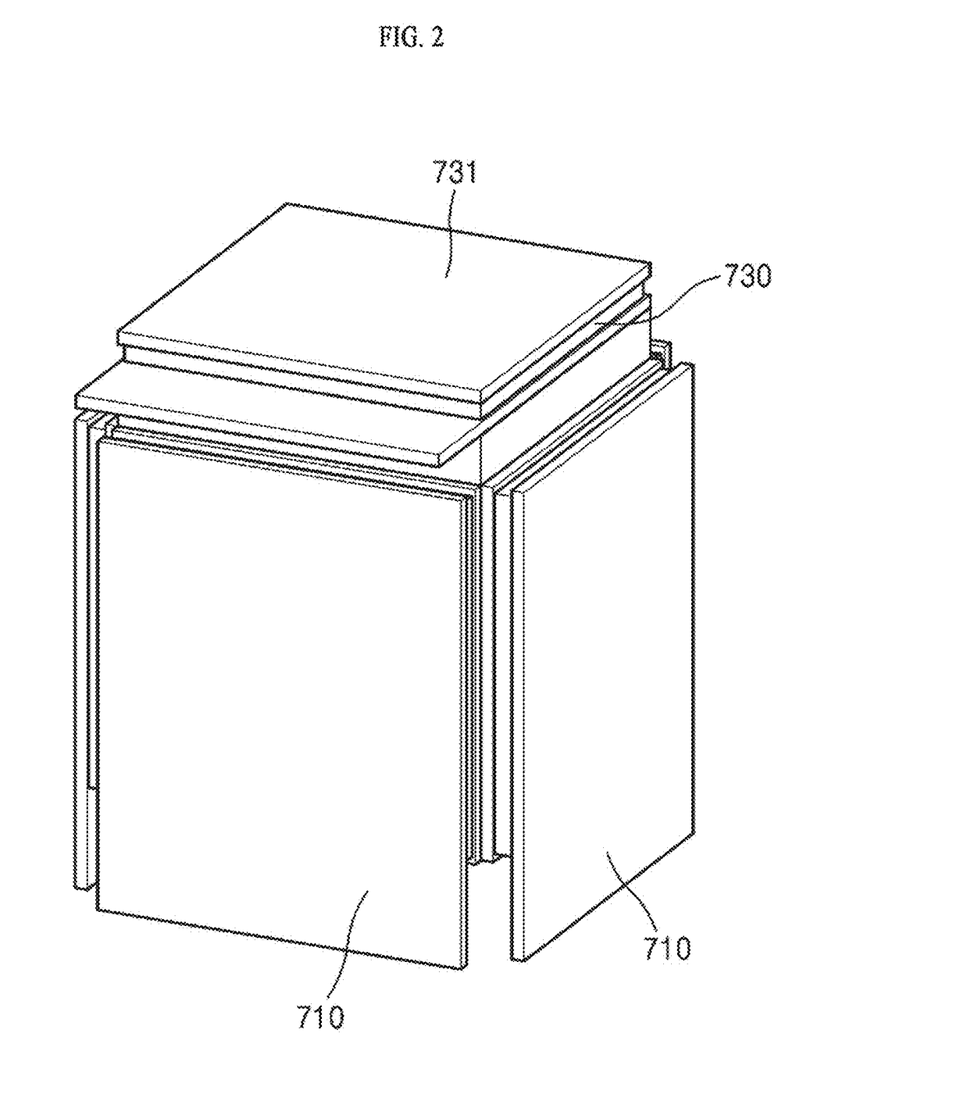
FIG. 2 is an example perspective view of the cooling generator shown in FIG. 1 according to some embodiments.
Figure 3:
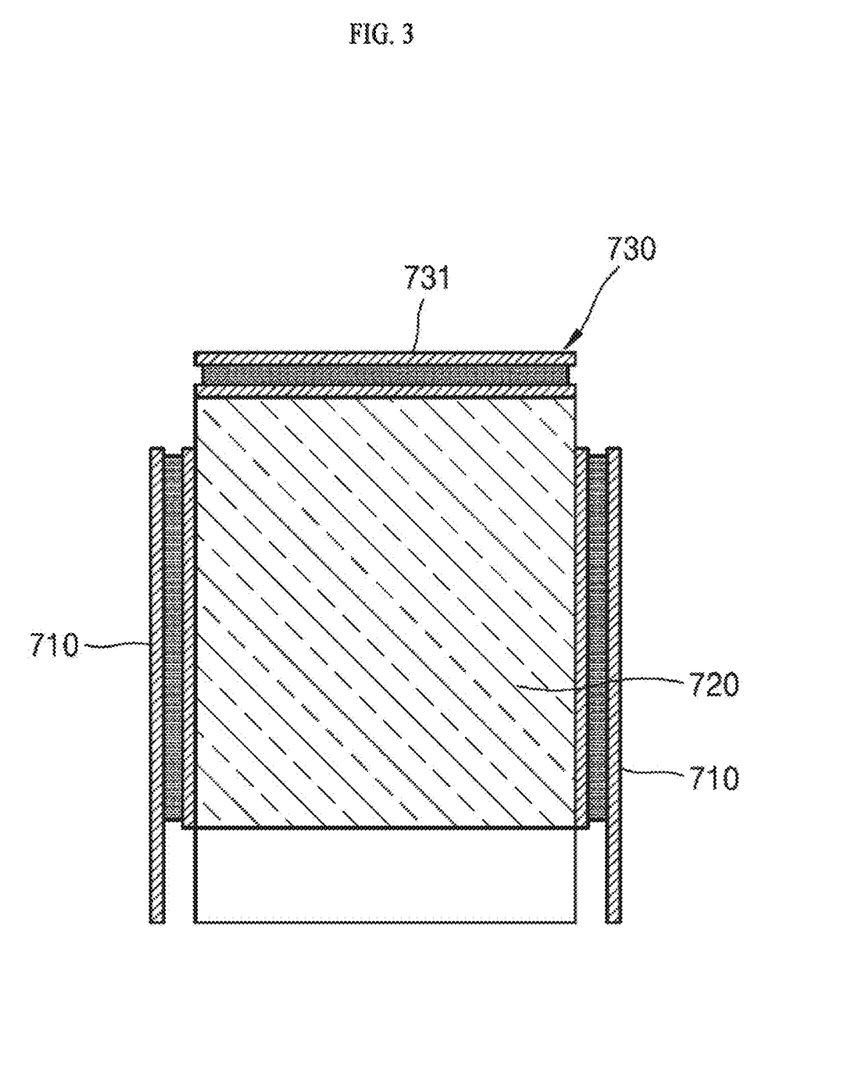
FIG. 3 is an example cross-sectional view of the cooling generator shown in FIG. 1 according to some embodiments.
Figure 4:
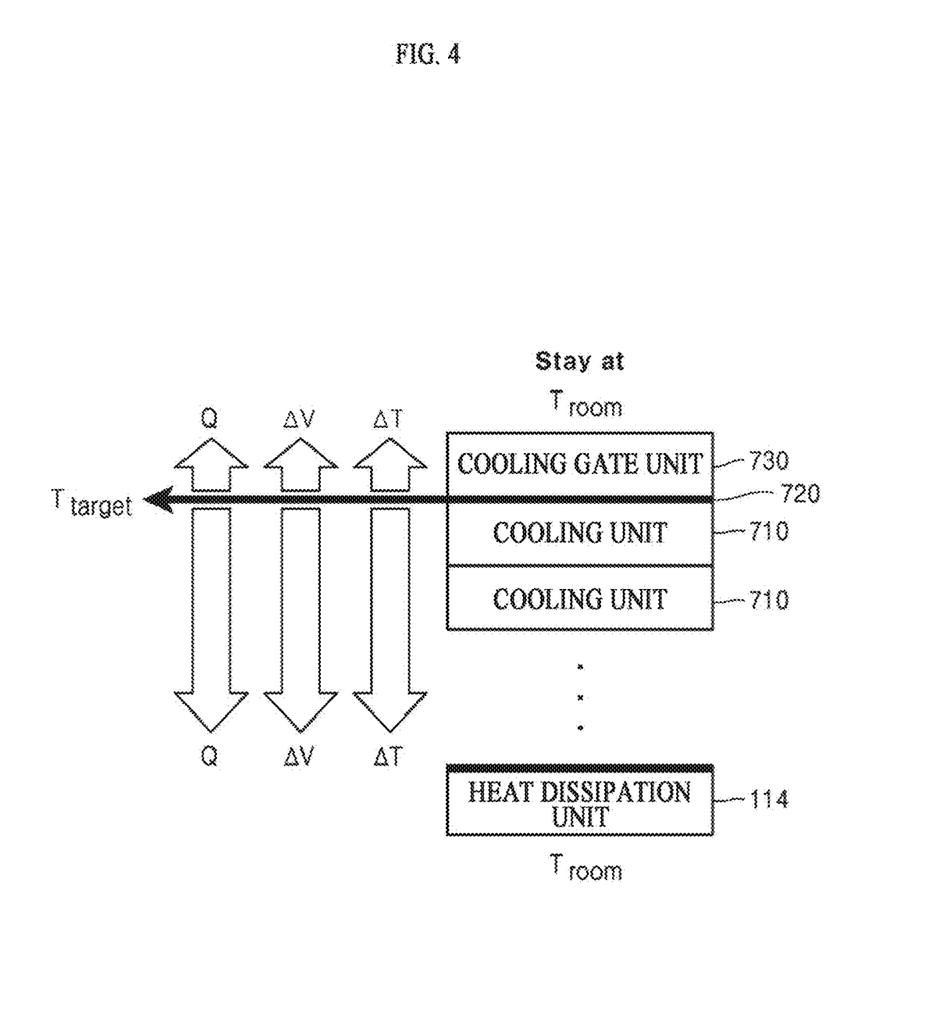
FIG. 4 is a view illustrating an operation of accumulating by the cooling generator of FIG. 1 according to some embodiments.
Figure 5:
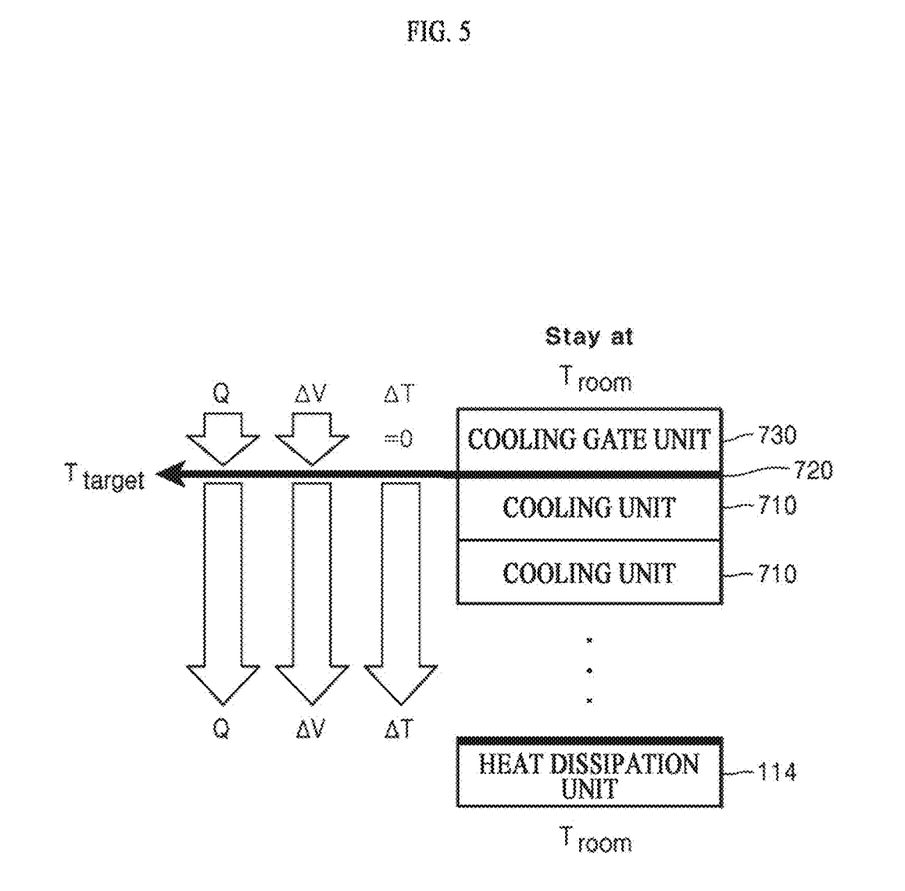
FIG. 5 is a view illustrating an operation of emitting cooling energy by the cooling generator of FIG. 1 according to some embodiments.

FIG. 1 is a block diagram illustrating the cooling generator 70 according to one embodiment, FIG. 2 is a perspective view schematically illustrating one example of the cooling generator 70 of FIG. 1, and FIG. 3 is a cross-sectional view of the cooling generator 70 of FIG. 2. FIG. 4 is a view illustrating an operation of accumulating, by the cooling generator 70 of FIG. 1, cooling energy to a cooling energy accumulation temperature, and FIG. 5 is a view illustrating an operation of emitting, by the cooling generator 70 of FIG. 1, cooling energy.

Referring to FIGS. 1 to 3, the cooling generator 70 may include a cooling unit (or a cooler) 710, a cooling accumulation unit (or a cooling accumulator) 720, a cooling gate unit (or a cooling gate) 730, and a control unit 740, Here, the control unit 740 may be a component included in the cooling generator 70 but is not limited thereto and may be a component equal to a control unit of a medical cooling apparatus 10.

The cooling unit 710 may generate cooling energy and supply the cooling energy to the cooling accumulation unit 720. The cooling unit 710 may have any forms capable of supplying cooling energy to the cooling accumulation unit 720 and include one or more cooling elements capable of generating cooling energy. The cooling unit 710 may generate cooling energy using at least one of a thermoelectric element (Peltier element) method, a phase change method, a Joule-Thomson method, a method of using thermodynamic cycle such as a Stirling cooler or a vapor compression refrigeration cycle. Otherwise, the cooling unit 710 may generate cooling energy using liquid evaporation or liquid nitrogen. Hereinafter, for convenience of description, a thermoelectric element will be mainly described. When the cooling unit 710 uses a thermoelectric element, heat generated by the thermoelectric element may be transferred to a heat dissipation unit 114 such as a heat sink and be discharged outward.

The cooling unit 710 may be thermally coupled with the cooling accumulation unit 720 and maintain a temperature of the cooling accumulation unit 720 at a preset cooling energy accumulation temperature. One or more cooling units 710 may be provided to be arranged on at least one surface of the cooling accumulation unit 720. For example, the cooling units 710 may be disposed on all surfaces excluding an area in which the cooling gate unit 730 among the cooling accumulation unit 720 is disposed. Otherwise, as shown in FIG. 2, the cooling units 710 may be arranged on all surfaces except the area in which the cooling gate unit 730 is disposed and an area opposite thereto. The concept of the present invention is not limited to the above structures, and any structures capable of efficiently transferring cooling energy to the cooling accumulation unit 720 are applicable thereto.

The cooling accumulation unit 720 may receive cooling energy generated by the cooling unit 710 and accumulate the cooling energy to become a preset cooling energy accumulation temperature. The cooling accumulation unit 720 may perform a function of a heat reservoir for cooling energy. The cooling accumulation unit 720 may receive cooling energy from the one or more cooling units 710 arranged on at least one surface. Here, due to the cooling gate unit 730 which will be described, the cooling energy is not emitted outward and accumulated to a cooling energy accumulation temperature. Here, a cooling energy accumulation temperature of the cooling accumulation unit 720 may be lower than room temperature.

The cooling accumulation unit 720 may include a metal material having high specific heat and thermal conductivity so as to efficiently transfer and accumulate cooling energy provided from the cooling unit 710. For example, the cooling accumulation unit 720 may include gold (Ag), silver (Au), copper (Cu), aluminum (Al), and the like.

The cooling accumulation unit 720 may have a form capable of efficiently accumulating cooling energy. As one embodiment, the cooling accumulation unit 720 may have a polyhedral structure. As shown in FIG. 2, the cooling accumulation unit 720 may be a hexahedron. Otherwise, the cooling accumulation unit 720 may have a cylindrical shape. The cooling accumulation unit 720 may be coupled with the cooling units 710 arranged on at least one surface thereof.

The cooling gate unit 730 may emit cooling energy accumulated in the cooling accumulation unit 720 outward or may block the accumulated cooling energy from being emitted outward. In detail, when cooling is performed by emitting the cooling energy accumulated at the cooling accumulation unit 720 outward, the cooling gate unit 730 may perform passive cooling of transferring cooling energy collected at the cooling accumulation unit 720 to a target area and active cooling performed using cooling energy generated in the cooling gate unit 730 at the same time. The cooling gate unit 730 may perform active cooling or active heating. Here, the cooling gate unit 730 may perform active cooling or active heating using a thermoelectric element (Peltier element) method.

As described above, the Peltier effect means a phenomenon in which when some types of metals are paired and currents are applied thereto, one contact point generates heat and the other contact point absorbs heat (cool). That is, in the Peltier effect, when direct current electricity is applied to a circuit including two different metals having the same forms, heat absorption occurs at one joint part and heat generation occurs at the other joint part. When currents are applied in an opposite direction, heat absorption and heat generation may occur in reverse.

The cooling energy unit 730 may control a direction of currents using thermoelectric elements having the Peltier effect so as to perform cooling or heating on an action surface 731. Here, the action surface 731 may be thermally coupled with an object to be cooled. The cooling gate unit 730 may actively block the cooling energy accumulated at the cooling accumulation unit 720 through active heating.

Meanwhile, the cooling gate unit 730 may have cooling power which is smaller than cooling power of the cooling unit 710. The cooling gate unit 730 may perform cooling equal to that of the cooling unit 710 but may perform a function of a switch which actually blocks or emits cooling energy accumulated at the cooling accumulation unit 720.

The control unit 740 may independently control the cooling unit 710 and the cooling gate unit 730. The control unit 740 may control the cooling unit 710 to perform cooling and control the cooling gate unit 730 to perform active cooling or active heating.

Hereinafter, referring to FIGS. 4 and 5, a method of accumulating and emitting cooling energy by controlling, by the control unit 740, the cooling unit 710 and the cooling gate unit 730 will be described in detail.

Referring to FIG. 4, the control unit 740 performs a first cooling operation of cooling the cooling accumulation unit 720 to be at a cooling energy accumulation temperature $T_{target}$ by controlling the cooling unit 710.

In detail, the control unit 740 may control the cooling unit 710 to generate cooling energy. As one embodiment, the cooling unit 710 may be formed of a thermoelectric element; and the control unit 740 may control generation of cooling energy by applying currents to the cooling unit 710. The cooling energy generated by the cooling unit 710 may be transferred to the cooling accumulation unit 720.

Here, the control unit 740 may not allow cooling energy accumulated at the cooling accumulation unit 720 to be emitted outward using the cooling gate unit 730 disposed on one surface of the cooling accumulation unit 720. The cooling gate unit 730 may block cooling energy through passive cooling of blocking emission of the cooling energy without applying power or active heating of actively blocking cooling energy by applying power thereto. Hereinafter, for being distinguished from passive cooling during a cooling energy transfer process, passive cooling for blocking cooling energy will be referred to as first passive cooling and passive cooling in transferring cooling energy will be referred to as second passive cooling.

That is, according to a method of blocking cooling energy according to some embodiments, the accumulated cooling energy may not be emitted outward by controlling the first passive cooling or active cooling to be performed. In other words, the cooling gate unit 730 may generate cooling energy on a surface in contact with the cooling accumulation unit 720 like the cooling unit 710, and active heating may occur on the action surface 731 which is opposite thereto and comes into contact with an object to be cooled. For example, the control unit 740 may control the cooling gate unit 730 to maintain a temperature of the action surface 731 at room temperature.

Through this, cooling energy supplied to the cooling accumulation unit 720 is not emitted outward and is accumulated at the cooling accumulation unit 720 and reaches the target cooling temperature $T_{target}$ due to the accumulated cooling energy. The control unit 740 may maintain the cooling accumulation unit 720 at the target cooling temperature $T_{target}$ through the control.

Afterwards, referring to FIG. 5, the control unit 740 performs a second cooling operation of cooling an object to be cooled to the target cooling temperature $T_{target}$ by performing second passive cooling of releasing cooling from being blocked by controlling the cooling gate unit 730 or active cooling.

In detail, the control unit 740 may release cooling at the cooling gate unit 730 from being blocked or perform active cooling by allowing currents applied to the cooling gate unit 730 to flow in a direction opposite to that of the first cooling operation. In other words, in the cooling gate unit 730, cooling energy may be generated on the action surface 731 and heat may be generated on a surface opposite to the action surface 731.

A path through which cooling energy may be emitted is formed due to action of the cooling gate unit 730, and the cooling energy accumulated at the cooling accumulation unit 720 is instantaneously discharged to the action surface 731 of the cooling gate unit 730. Here, the second passive cooling performed by the accumulated cooling energy of the cooling accumulation unit 720 and passive cooling performed by the cooling gate unit 730 may occur on the action surface 731 of the cooling gate unit 730.

Through the above configuration, the cooling generator 70 may allow a temperature of an object to be cooled which comes into contact with the action surface 731 to instantaneously reach the target cooling temperature $T_{target}$. Also, as the cooling generator 70 approaches the cooling target temperature, the necessary power decreases and thus precision of cooling may be increased.

Meanwhile, to provide a low target cooling temperature, the cooling accumulation unit 720 may include a variety of operations.

Figure 6:
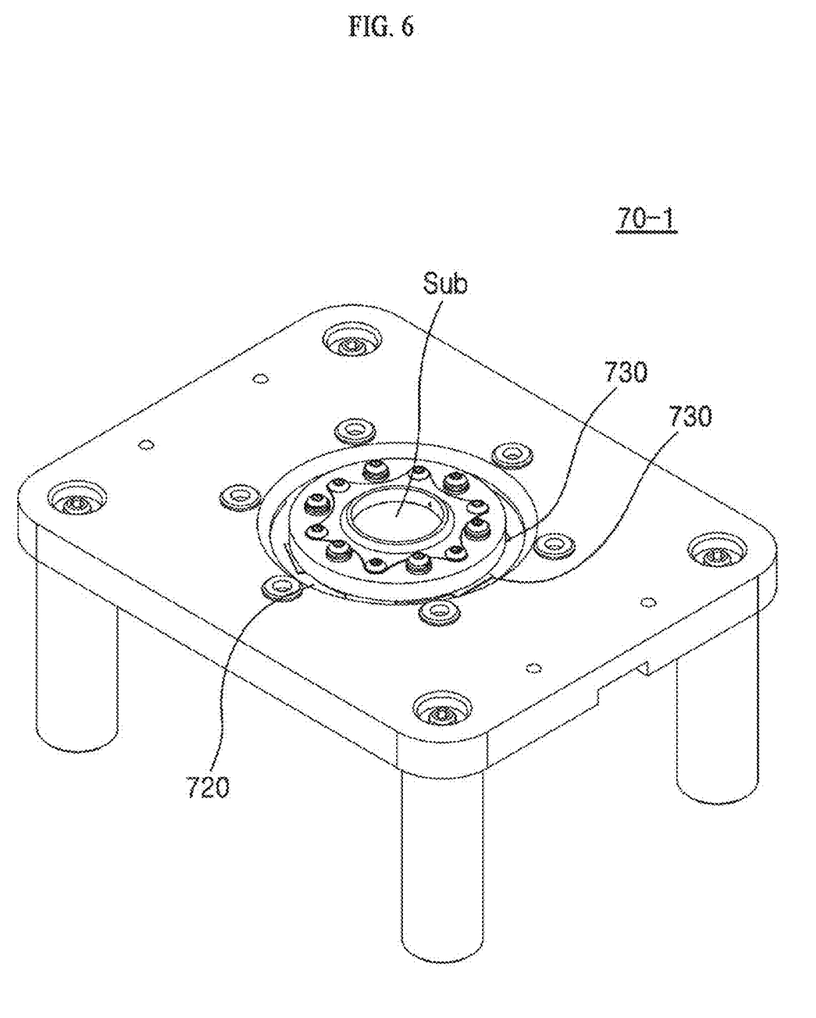
FIG. 6 is an example perspective view of another cooling generator according to some embodiments.
Figure 7:
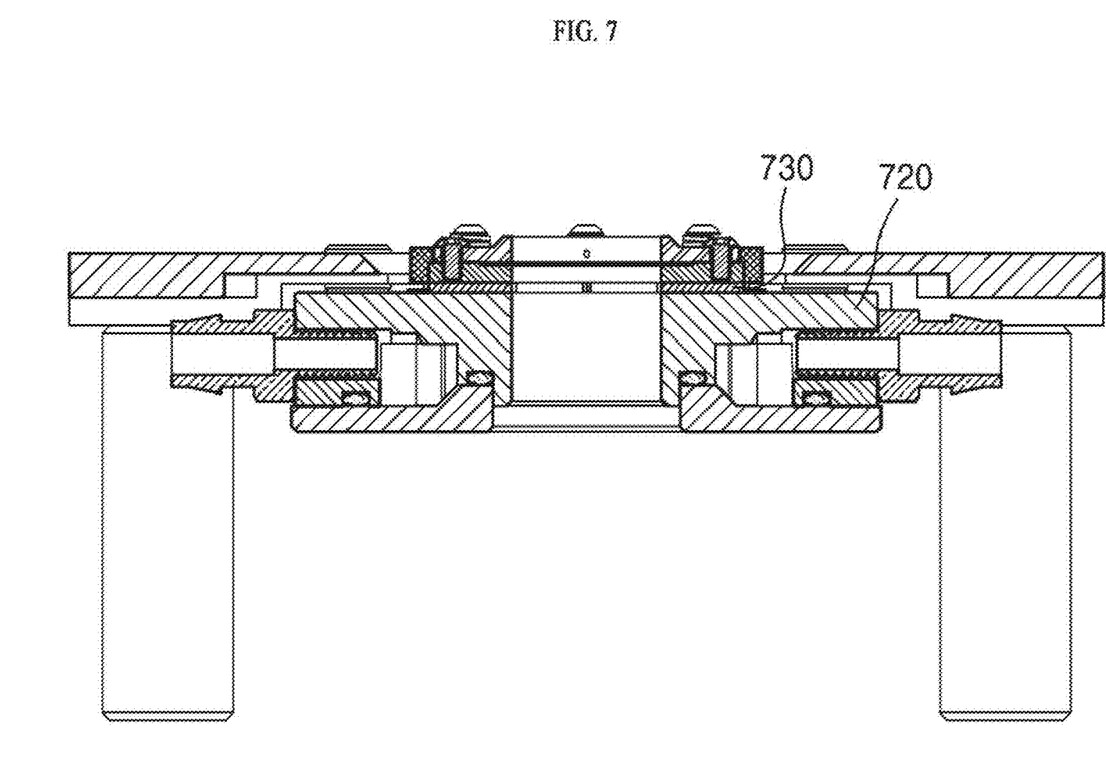
FIG. 7 is a cross-sectional view of the cooling generator shown in FIG. 6 according to some embodiments.
Figure 8:
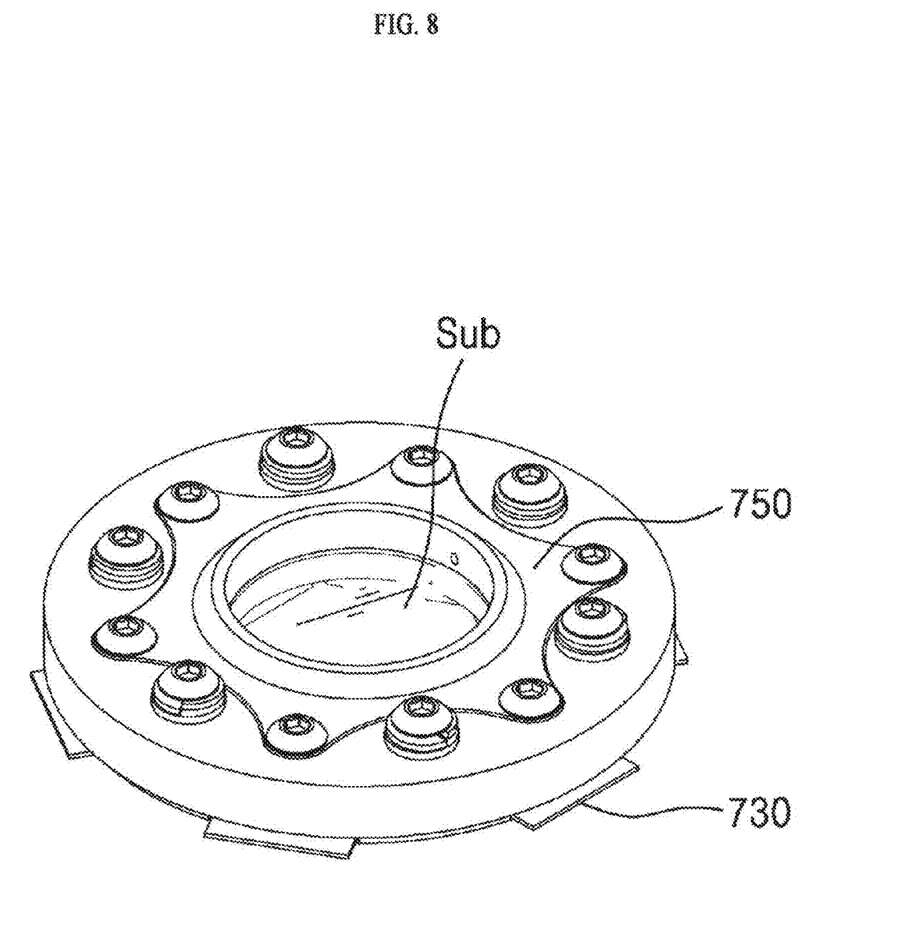
FIG. 8 is a view illustrating some components extracted from the cooling generator shown in FIG. 6 according to some embodiments.

FIG. 6 is a perspective view illustrating another embodiment of a cooling generator 70-1, FIG. 7 is a cross-sectional view illustrating the cooling generator 70-1 of FIG. 6, and FIG. 8 is a view illustrating some components extracted from the cooling generator 70-1 of FIG. 6.

Referring to FIGS. 1 and 6 to 8, the cooling generator 70-1 may include a substrate Sub, the cooling accumulation unit 720, the cooling gate unit 730, the control unit 740, and a cooling operation unit (a cooling operator) 750. Basically, the cooling generator 70-1 according to another embodiment performs cooling according to a principle which is the same as that of the above-described cooling generator 70, and a repetitive description will be omitted for convenience of description. Here, the cooling generator 70-1 according to another embodiment may include the cooling unit 710 but may cool the cooling accumulation unit 720 using a refrigerant which comes into contact with the cooling accumulation unit 720.

The cooling generator 70-1 according to another embodiment includes the cooling operation unit 750 surrounding the substrate Sub and has a feature of precisely cooling the substrate Sub at a target cooling temperature at high speed using the cooling gate unit 730 disposed between the cooling operation unit 750 and the cooling accumulation unit 720.

The substrate Sub may include a transparent material and may be formed of a diamond or sapphire material to increase heat conductivity.

The cooling operation unit 750 may be formed to surround the substrate Sub. Although it is shown in the drawing that a round opening is formed in a center of the cooling operation unit 750 and the substrate Sub is disposed in the opening, the concept of the present invention is not limited thereto and any forms capable of maximizing cooling efficiency are applicable thereto. For example, the opening of the cooling operation unit 750 may have a polygonal shape such as a quadrangular shape. The cooling operation unit 750 may be formed of a material having high heat conductivity to efficiently transfer cooling energy from the cooling gate unit 730.

The cooling accumulation unit 720 may be disposed to be adjacent to the cooling operation unit 750 with the cooling gate unit 730 interposed therebetween. The cooling accumulation unit 720 is thermally coupled with the cooling gate unit 730 and the cooling operation unit 750. The cooling accumulation unit 720 may be thermally coupled with the cooling unit 710 described above and receive cooling energy but may receive cooling energy by coming into contact with a refrigerant such as liquid nitrogen or a coolant. The cooling accumulation unit 720 may also include a material having high heat conductivity to efficiently transfer cooling energy. In detail, it is apparent that a target cooling energy accumulation temperature $T_{target}$ of the cooling accumulation unit 720 receiving cooling energy using liquid nitrogen is lower than a target cooling temperature. Herein, passive cooling increases such that an effect of increasing a cooling speed may be provided. That is, to increase the cooling speed, the cooling energy accumulation temperature $T_{target}$ may be set to be lower than the target cooling temperature.

The cooling gate unit 730 may be disposed between one surface of the cooling accumulation unit 720 and the cooling operation unit 750 and block the cooling energy accumulated in the cooling accumulation unit 720 from being emitted toward the cooling operation unit 750 or the substrate Sub. The cooling gate unit 730 may include a plurality of thermoelectric elements and be radially disposed as shown in the drawing. As another embodiment, the cooling gate unit 730 may include one thermoelectric element and block or emit cooling energy between the cooling accumulation unit 720 and the cooling gate unit 730.

Meanwhile, although not shown in the drawing, in the cooling generator 70-1 according to another embodiment, a temperature sensor (not shown) may be disposed in the cooling operation unit 750. In detail, the temperature sensor may be disposed on an opening surface of the cooling operation unit 750 and measure a temperature of a boundary gas (surrounding air) round the substrate Sub. The temperature sensor may be a micro temperature sensor having a small thermal capacity.

The cooling generator 70-1 having the above structure may instantaneously and precisely cool the substrate Sub at the target cooling temperature by performing the first cooling operation at the cooling accumulation unit 720 and the second cooling operation at the cooling gate unit 730. Since the cooling generator 70-1 can instantaneously cool not only the substrate Sub but also a boundary gas on the substrate Sub, the cooling generator 70-1 may perform a function of an instantaneous boundary air cooler. For example, an air chamber capable of holding cooled air may be formed by forming the cooling operation unit 750 on a surface of the substrate Sub in a circumferential direction. The instantaneous boundary air cooler may minimize a heat loss caused by a convection current by cooling the boundary gas around the substrate Sub so as to maximize cooling of the substrate Sub.

Figure 9:
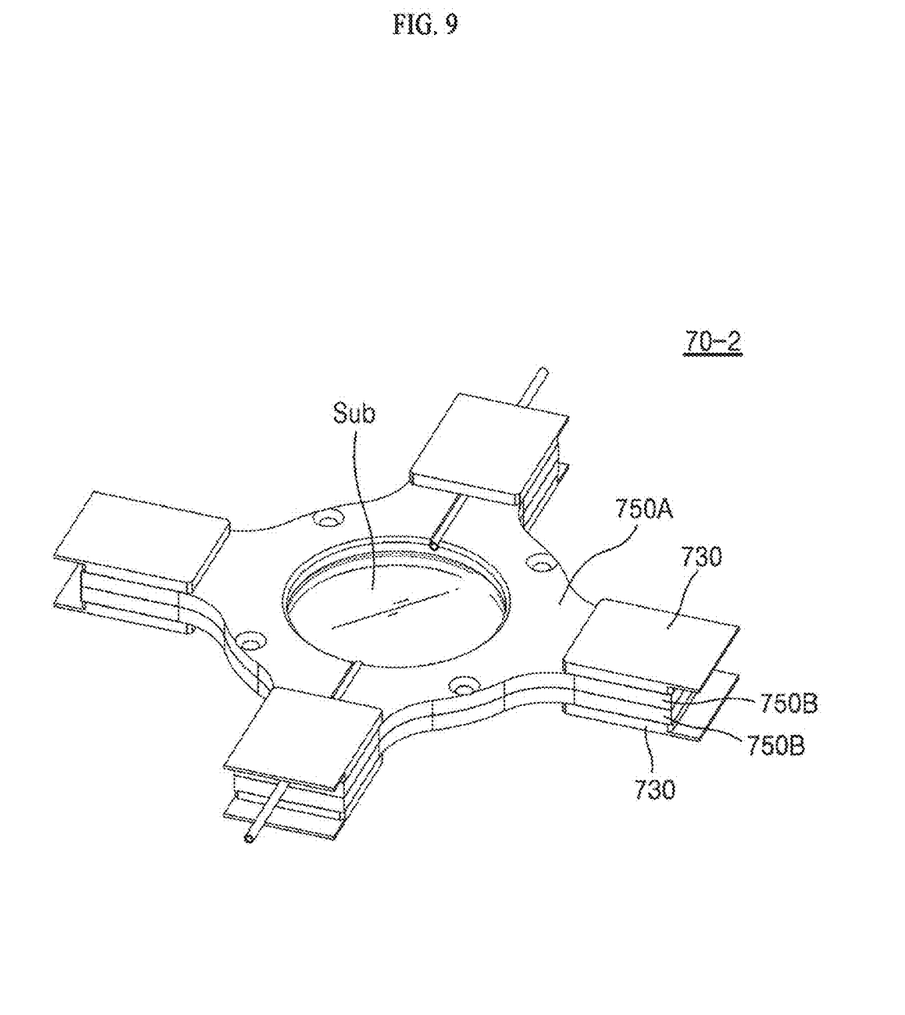
FIG. 9 is an example perspective view of another cooling generator according to some embodiments.
Figure 10:
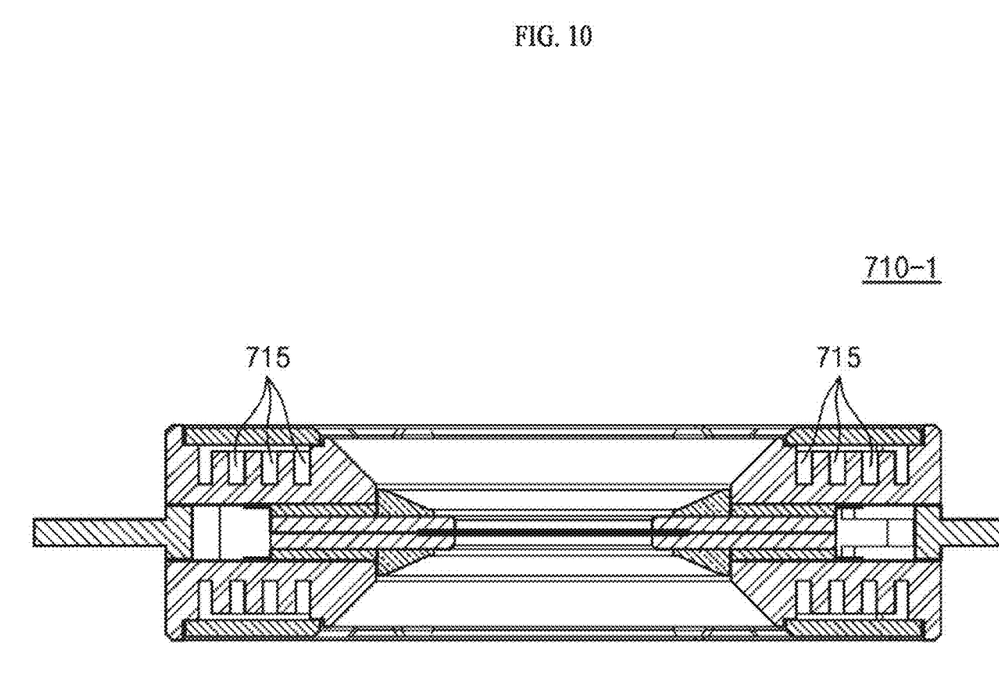
FIG. 10 is a cross-sectional view of a cooling unit according to some embodiments.

FIG. 9 is a perspective view illustrating still another embodiment of the cooling generator of FIG. 1, and FIG. 10 is a cross-sectional view illustrating another embodiment of the cooling unit.

Referring to FIGS. 9 and 10, a cooling generator 70-2 may include a substrate Sub, a cooling unit 710-1, the cooling gate unit 730, the control unit 740, and the cooling operation unit 750. The cooling generator 70-2 according to still another embodiment performs cooling according to a principle equal to those of the above-described cooling generators 70 and 70-1, and a repetitive description will be omitted for convenience of description.

The cooling generator 70-2 according to still another embodiment may include the cooling operation unit 750 surrounding the substrate Sub. Here, the cooling operation units 750 may be disposed on both sides with the substrate Sub interposed therebetween. In detail, the cooling operation units 750 may be provided as two cold plates disposed above and below the substrate Sub, and the two cold plates may each include a central area 750A surrounding the substrate Sub and one or more arm areas 750B extending from the central area to an outer part. The central area 750A may include an opening which exposes a part of the substrate Sub outward as shown in the drawings. Meanwhile, as shown in the drawings, the cooling operation unit 750 may include four arm areas 7509 extending in four directions.

The cooling gate unit 730 may be disposed in the arm area 7509 of the cooling operation unit 750. Here, as shown in the drawings, the cooling gate unit 730 may be disposed on one surface of the arm area 750B exposed outward. In the drawings, although it is shown that the cooling gate units 730 are disposed on a top surface and a bottom surface of the arm area 750B, the cooling gate unit 730 may be disposed on a side surface of the arm area 750B. The cooling gate unit 730 may be disposed between the cooling unit 710-1 and the cooling operation unit 750 and block the cooling energy generated from the cooling unit 710-1 and accumulated from being emitted toward the cooling operation unit 750 or the substrate Sub. The cooling gate unit 730 may include a thermoelectric element and be disposed in each of the arm areas 750B of the cooling operation unit 750.

Also, the cooling unit 710-1 according to another embodiment may generate and accumulate cooling energy at the same time. For example, the cooling unit 710-1 may be formed of a water block in which a refrigerant such as a coolant continuously flows through a flow path 715 formed therein and generates cooling energy. Here, the water block may perform a function of accumulating cooling energy, by itself, due to the coolant which continuously flows.

The cooling units 710-1 may be disposed to be opposite to the cooling operation unit 750, in detail, the arm area 750B of the cooling operation unit 750 with the cooling gate unit 730 interposed therebetween. Particularly, as shown in the drawings, the cooling generator 70-2 according to still another embodiment may structurally include a sandwich structure in which the cooling unit 710-1, the cooling gate unit 730, the cooling operation unit 750, the substrate Sub, the cooling operation unit 750, the cooling gate unit 730, and the cooling unit 710-1 are sequentially arranged, and the sandwich structure may be coupled by coupling the cooling units 710-1 arranged outermost. As one embodiment, the cooling units 710-1 may be connected through screw coupling. Through this, cooling energy generated from the cooling units 710-1 may not directly transferred to the substrate Sub or the cooling operation unit 750, and the cooling generator 70-2 may minimize a heat leakage.

As described above, in the cooling generator 70-2 according to still another embodiment, cooling efficiency may be maximized by arranging one or more cooling gate units 730 on the cooling operation unit 750, and more particularly, arranging one or more cooling gate units 730 opposite to one arm area 750B.

Although embodiments have been described above with reference to the drawings, these are merely examples and it should be understood by one of ordinary skill in the art that a variety of modifications and changes may be made. Accordingly, the technical scope of the present invention should be determined by the technical concept of the following claims.

According to embodiments of the present invention, there is provided a cooling apparatus for medical or life science experiments. Also, the disclosed embodiments are applicable to cooling apparatuses and the like which are used industrially.

What is claimed is:

1. An apparatus for generating refrigeration comprising,
a cooling accumulator configured to accumulate cooling energy;
a cooler thermally connected to the cooling accumulator and configured to cool the cooling accumulator;
a cooling gate configured to selectively block or allow transmission of the cooling energy accumulated in the cooling accumulator to a target, the cooling gate comprising a first surface in direct physical contact with the cooling accumulator and a second surface opposing the first surface; and
a controller configured to:
perform a first cooling operation of cooling the cooling accumulator to a target cooling temperature $T_{target}$ by controlling the cooler to generate the cooling energy such that the cooling energy is transferred from the cooler to the cooling accumulator;
control the cooling gate to generate cooling energy on the first surface thereof and heat the second surface such that the cooling energy accumulated in the cooling accumulator is not transferred from the cooling accumulator to the cooling gate; and
perform a second cooling operation of cooling the target to the target cooling temperature $T_{target}$ by controlling the cooling gate such that the cooling energy accumulated in the cooling accumulator is transferred from the cooling accumulator to the second surface of the cooling gate configured to contact the target.

2. The apparatus for generating refrigeration of claim 1, wherein the cooler is configured to work through at least one of a Peltier effect, a phase change effect, a Joule-Thomson effect or a thermodynamic cycle.

3. The apparatus for generating refrigeration of claim 1, wherein the cooler has a cooling output greater than a cooling output of the cooling gate.

4. The apparatus for generating refrigeration of claim 3, wherein the cooling accumulator is polyhedral, and wherein a plurality of faces of the cooling accumulator are configured to thermally connect to a cooling element included in the cooler.

5. The apparatus for generating refrigeration of claim 3, wherein the cooling accumulator comprises a face configured to thermally connect to a cooling element included in the cooler.

6. A cooling method, comprising,
providing a cooling apparatus that comprises:
a cooling accumulator configured to accumulate cooling energy,
a cooler thermally connected to the cooling accumulator and configured to cool the cooling accumulator,
a cooling gate configured to selectively block or allow transmission of the cooling energy accumulated in the cooling accumulator to a target, the cooling gate comprising a first surface in direct physical contact with the cooling accumulator and a second surface opposing the first surface, and
a controller;
performing, by the controller, a first cooling operation of cooling the cooling accumulator to a target cooling temperature $T_{target}$ by controlling the cooler to generate the cooling energy such that the cooling energy is transferred from the cooler to the cooling accumulator; and
controlling, by the controller, the cooling gate to generate cooling energy on the first surface thereof and heat the second surface such that the cooling energy accumulated in the cooling accumulator is not transferred from the cooling accumulator to the cooling gate;
performing a second cooling operation of cooling a target to the target cooling temperature $T_{target}$ by controlling the cooling gate such that the cooling energy accumulated in the cooling accumulator is transferred from the cooling accumulator to the second surface of the cooling gate configured to contact the target.

7. An apparatus for generating refrigeration, comprising,
a substrate on which cooling is configured to be performed;
a cooling accumulator configured to accumulate cooling energy;
a plurality of coolers thermally connected to the cooling accumulator and configured to cool the cooling accumulator;
a plurality of cooling gates configured to selectively block and allow transmission of the cooling energy to the substrate, each of the plurality of cooling gates comprising a first surface in direct physical contact with the cooling accumulator and a second surface opposing the first surface;

a cooling operator including an opening which exposes a portion of the substrate, and configured to thermally transfer the cooling energy transmitted through the plurality of cooling gates to the substrate; and, a controller configured to:

perform a first cooling operation of cooling the cooling accumulator to a target cooling temperature $T_{target}$ by controlling the plurality of coolers to generate the cooling energy such that the cooling energy is transferred from the plurality of coolers to the cooling accumulator;

control each of the plurality of cooling gates to generate cooling energy on the first surface thereof and heat the second surface such that the cooling energy accumulated in the cooling accumulator is not transferred from the cooling accumulator to the plurality of cooling gates; and perform a second cooling operation of cooling the substrate to the target cooling temperature $T_{target}$ by controlling the plurality of cooling gates such that the cooling energy accumulated in the cooling accumulator is transferred from the cooling accumulator to the second surface of each of the plurality of cooling gates configured to contact the cooling operator.

8. The apparatus for generating refrigeration of claim 1, wherein during the first cooling operation, the controller is configured to apply a first current flowing in a first direction to the cooling gate such that the target is maintained at a temperature different from the target cooling temperature $T_{target}$, and wherein, during the second cooling operation, the controller is configured to apply a second current, flowing in a second direction opposite to the first direction, to the cooling gate.

9. The apparatus for generating refrigeration of claim 1, wherein the controller is configured to maintain a temperature of the cooling accumulator at the target cooling temperature $T_{target}$ until the second cooling operation is performed.

10. The apparatus for generating refrigeration of claim 1, wherein the cooling accumulator comprises a metal matrix comprising at least one of gold, silver, copper, or aluminum.

11. The apparatus for generating refrigeration of claim 1, wherein the cooling accumulator comprises a block with a fluid channel containing a fluid continuously flowing therethrough.

12. The apparatus for generating refrigeration of claim 1, wherein the cooling accumulator comprises a top wall and a plurality of sidewalls extending from the top wall, wherein the cooling gate is attached to the top wall, wherein the cooler comprises a plurality of cooler elements, each being attached to one of the plurality of sidewalls.

13. The cooling method of claim 6, wherein performing the first cooling operation comprises applying a first current flowing in a first direction to the cooling gate such that the target is maintained at a temperature different from the target cooling temperature $T_{target}$, and wherein performing the second cooling operation comprises applying a second current, flowing in a second direction opposite to the first direction, to the cooling gate.

\* \* \* \* \*